United States Patent [19]

Ohnuma et al.

[11] Patent Number: 5,506,269
[45] Date of Patent: Apr. 9, 1996

[54] PARASITICIDE EMPLOYING PYRETHROID TYPE COMPOUNDS

[75] Inventors: Kazutomi Ohnuma, Mobara; Masahiko Nakamura, Yokohama; Takashi Fujita, Chiba; Takatoshi Udagawa, Mobara, all of Japan

[73] Assignee: Mitsui Toatsu Chemicals, Inc., Tokyo, Japan

[21] Appl. No.: 361,495

[22] Filed: Dec. 22, 1994

[30] Foreign Application Priority Data

Dec. 27, 1993 [JP] Japan ................................. 5-331983

[51] Int. Cl.$^6$ .......................... A01N 31/14; A01N 37/34; A01N 53/00
[52] U.S. Cl. ...................... 514/721; 514/521; 514/531
[58] Field of Search ............................................... 514/721

[56] References Cited

U.S. PATENT DOCUMENTS 4,397,864  8/1983  Nakatani et al. ....................... 424/282
4,864,027  9/1989  Shubert et al. ........................... 546/14

FOREIGN PATENT DOCUMENTS

| 068297 | 1/1983 | European Pat. Off. . |
| 224024 | 6/1987 | European Pat. Off. . |
| 354761 | 2/1990 | European Pat. Off. . |
| 3731609 | 3/1989 | Germany . |
| 3828339 | 3/1990 | Germany . |
| 2187452 | 9/1987 | United Kingdom . |
| WOA8607525 | 12/1986 | WIPO . |

OTHER PUBLICATIONS

Recent Advances In The Chemistry Of Insect Control, "A New Type Of Synthetic Pyrethroid Insecticide", T. Udagawa et al, Cambridge, England, 1984, pp. 192–204.

*Primary Examiner*—Allen J. Robinson
*Attorney, Agent, or Firm*—Burns, Doane, Swecker & Mathis

[57] ABSTRACT

The present invention discloses a parasiticide comprising, as the active ingredient, at least one natural or synthetic pyrethroid type compound.

4 Claims, No Drawings

PARASITICIDE EMPLOYING PYRETHROID TYPE COMPOUNDS

BACKGROUND OF THE INVENTION

The present invention relates to a parasiticide for endoparasites, comprising, as the active ingredient, at least one natural or synthetic pyrethroid type compound, and to a method for exterminating endoparasites, which comprises orally or percutaneously administering said parasiticide.

In general, parasite diseases are caused when parasites, i.e. unicellular protozoans (Protozoa), multicellular Helminths, anthropods, etc. are parasitic on an animal host. It is reported that, in Japan, parasite diseases have decreased remarkably owing to the improvement in environmental hygiene and that the diseases are in wide spread worldwide, particularly in developing countries, giving considerable damage in these countries. However, in recent years, even in the developed countries, parasite diseases are beginning to increase owing to (1) the infection of long- or short-term travellers to developing countries, (2) the infection from imported foods or from the raw meat, raw fish and raw foods made available by the development of refrigeration and transportation techniques, and (3) the infection from pets.

Further, there is now a problem of opportunistic infection of parasites because non-pathogenic or low-pathogenic parasites come to aquire pathogenicity within a person who becomes immunodeficient owing to (1) the use of a large amount of drugs such as immunosuppressant and carcinostatic and (2) infective disease such as AIDS.

In addition, parasite diseases pose a general and serious economic problem in domestic animals such as pig, horse, cattle, sheep, goat, dog, cat, fowls.

The animals infected with parasite diseases incur anemia, malnutrition, asthenia, weight loss and serious damages of intestinal paries and other tissues and organs, which causes reduction in feed efficiency or productivity and invites a large economic loss. Thus, it is a long-standing important task to develop a novel parasiticidal or antiprotozoan agent.

SUMMARY OF THE INVENTION

The present invention has been made in view of the above task and is intended to provide a parasiticide for exterminating endoparasites parasitic on humans and animals.

Natural or synthetic pyrethroid type compounds are very safe to humans and animals although they are active to insects which are harmful to agriculture, sanitation, wood and forest, and foods. Hence, in order to achieve the above intention, the present inventors made a study to examine whether or not the above compounds are capable of exterminating endoparasites when directly applied to humans and animals. As a result, the present inventors have found out that the compounds can efficiently exterminate endoparasites when administered orally or percutaneously. The finding has led to the completion of the present invention.

The present invention provides a parasiticide comprising, as the active ingredient, at least one natural or synthetic pyrethroid type compound.

The parasiticide of the present invention can efficiently exterminate endoparasites parasitic on humans and animals, thereby can prevent or treat parasite diseases.

DETAILED DESCRIPTION OF THE INVENTION AND PREFERRED EMBODIMENTS

The natural or synthetic pyrethroid type compound according to the present invention is a known pyrethroid type compound. Specific examples thereof are acrinathrin: (S)-α-cyano-3-phenoxybenzyl (Z)-(1R,3S)-2,2-dimethyl-3-[2-(2,2,2-trifluoro-1-trifluoromethylethoxycarbonyl)vinyl]cyclopropanecarboxylate, allethrin: (RS)-3-allyl-2-methyl-4-oxocyclopentenyl (1RS)-cis,trans-chrysanthemate, alpha-cypermethrin: α-cyano-3-phenoxybenzyl 3-(2,2-dichlorovinyl)-2,2-dimethylcyclopropanecarboxylate, cycloprothrin: (RS)-α-cyano3-phenoxybenzyl (RS)-2,2-dichloro-1-(4-ethoxyphenyl)cyclopropanecarboxylate, cyfluthrin: (RS)-α-cyano-4-fluoro-3-phenoxybenzyl (1RS, 3RS:1RS,3SR)-3-(2,2-dichlorovinyl)-2,2-dimethylcyclopropanecarboxylate, cyphenothrin: (RS)-α-cyano-3-phenoxybenzyl (1R)-cis,transchrysanthemate, empenthrin: (RS)-1-ethyl-2-methyl-2pentenyl (1R)-cis,trans-chrysanthemate, fenvalerate: (RS)-α-cyano-3-phenoxybenzyl (RS)-2-(4-chlorophenyl)-3methylbutyrate, kadethrin: 5-benzyl-3-furylmethyl (E)-(1R,3S)-2,2-dimethyl-3-(2-oxothiolane-3-indenemethyl)-cyclopropanecarboxylate, permethrin: 3-phenoxybenzyl (1RS)-cis,trans-3-(2,2-dichlorovinyl)-2,2-dimethylcyclopropanecarboxylate, phenothrin: 3-phenoxybenzyl 2,2-dimethyl-3-(2-methylpropenyl)cyclopropanecarboxylate, prallethrin: (S)-2-methyl-4-oxo-3-(2-propinyl)-cyclopentenyl (1R)-cis,trans-chrysanthemate, resmethrin: 5-benzyl-3-furylmethyl (1RS)-cis,trans-chrysanthemate, tetramethrin: cyclohexene-1,2-dicarboximidomethyl (1RS)-cis,trans-2,2-dimethyl-3-(2-methylpropenyl)cyclo-propanecarboxylate, tralomethrin: (S)-α-cyano-3-phenoxybenzyl (1R,3S)-2,2-dimethyl-3-[(RS)tetrabromoethyl]-cyclopropanecarboxylate, pyrethrin, and a synthetic pyrethroid compound represented by general formula (1)

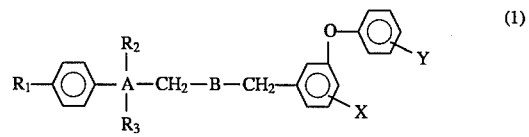

wherein $R_1$ represents a lower alkyl group, a lower alkoxy group or a lower haloalkoxy group; $R_2$ represents a lower alkyl group or a lower haloalkyl group; represents a lower alkyl group or a hydrogen atom; A represents a carbon atom or a silicon atom; B represents an oxygen atom or $CH_2$; X represents a hydrogen atom or a halogen atom; and Y represents a hydrogen atom or a halogen atom.

The synthetic pyrethroid type compound represented by general formula (1) is particularly preferable as the present parasiticide for endoparasites, in view of the safety to humans and animals. The compound represented by general formula (1) includes, for example, flufenprox: [3-(4-chlorophenoxy)benzyl] (RS)-2-(4-ethoxyphenyl)-3,3,3-trifluoropropyl ether, SSI-116: dimethyl(4-ethoxyphenyl)silylmethyl 3-phenoxybenzyl ether, HOE-498: (4-ethoxyphenyl)[3-(4-fluoro-3-phenoxyphenyl)propyl] (dimethyl) silane, etofenprox: 2-(4-ethoxyphenyl)-2-methylpropyl 3-phenoxybenzyl ether, halfenprox: 2-[4-(bromodifluoromethoxy)phenyl]-2-methylpropyl 3-phenoxybenzyl ether, MTI-790: 1-(3-phenoxy-phenyl)-4-(4-ethoxyphenyl)-4-methylpentane, and MTI800: 1-(3-phenoxy-4-fluorophenyl)-4-(4-ethoxyphenyl)-4-methylpentane.

Etofenprox, MTI-790, MTI-800, SSI-116 and HOE-498 are particularly preferable in view of the activity to endoparasites and the safety to humans and animals.

The humans and animals to which the present invention is applicable, are humans; domestic animals such as pig, horse, cattle, sheep, goat, rabbit, camel, buffalo, deer, mink and chinchilla; domestic fowls such as fowl, duck, goose and turkey; pets such as dog, cat, small bird and monkey; and experimental animals such as rat, mouse, golden hamster and guinea pig.

The ordinary endoparasites which are parasitic on humans and to which the present compound is effective, are roughly divided into Protozoa and Helminths. Protozoa includes Rhizopoda such as Entamoeba; Zoomastigophora such as Leishmania, Trichomonas and Plasmodium (malaria parasite); and Ciliata such as *Balantidium coli*. Helminths includes Nematoda such as Ascaris, Toxocare, Anisakis, Enterobius, Ancylostoma, Trichostrongylus, Angiostrongylus, Trichuris, Strongyloides, Gnathostoma, Wuchereria, Bruqia, Onchocerca, Loa, Mansonella and Dirofilaria; Acanthocephala and Trematoda such as Schistosoma, Fasciola, Clonorchis, Opisthorchis, Eurytrema, Paragonimus, Metagonimus, Heterophyes, Fasciolopsis and Echinostoma;, and Cestoda such as Diphyllobothrium, Taenia and Echinococcus.

The ordinary endoparasites which are parasitic on animals and to which the present compound is effective, are Nematoda such as Ascaris, Toxocara, Toxascaris, Parascaris, Ascaridia, Heterakis, Oxyuris, capillaria, Trichinella, Stronqylus, Triodontophorus, Trichonema, Stephanurus, Desophogostomum, Chabertia, Syngamus, Ancyostoma, Uncinaria, Necator, Bunostomum, Trichostrongylus, Cooperia, Nematodirus, Haemonchus, Ostertagia, Dictyocaulus, Metastrongylus, Dirofilaria, Parafilaria, Setaria, Onchocerca, Habronema, Arduenna and Acuaria; Cestoda such as Diphyllobothrium, Anoplocephara, Moniezia, Dipylidium, Taenia, Dithyridium, Raillietina and Echinococcus; Trematoda such as Schistosoma, Paramphistomum and Fasciola; and other various parasites.

The parasiticide for endoparasites according to the present invention is effective not only to parasites parasitic on the bodies of intermediate hosts and final hosts but also to parasites parasitic on the bodies of reservoir hosts. Further, the present parasiticide for endoparasites is effective for all the growth stages of parasites. For example, the growth stages of protozoa include cyst, precyst, trophozoite, schizont in schizogony, ameboid form, gametocyte in syngenesis, macrogamete and microgamete, zygote and sporozoite; and the growth stages of Nematoda include egg, larva and adult.

Furthermore, the present compound not only can exterminate parasites present in the living bodies of hosts but also can prevent the infection with parasite diseases by application thereof to the environments which are the infection routes of said diseases. For example, the present parasiticide can prevent, in advance, soil infections from soils of upland fields and parks; percutaneous infections from aqueous systems (e.g. river, lake, wetland and paddy field); oral infections from excrements of animals such as dog and cat; and oral infections from raw meats of sea water fish, fresh water fish, Crustaceae, shellfish, domestic animals and the like; and infections from vermin such as mosquito, horsefly, fly, cockroach, tick, flea, louse, reduviid and trombidicula.

The parasiticide for endoparasites according to the present invention can be administered as a drug for humans or animals, for the purpose of cure or prevention of parasite diseases. The method of administration may be oral or parenteral. In the case of oral administration, the present parasiticide can be applied in the form of capsules, tablets, pills, a powder, granules, paryules, a syrup, an enteric agent, a suspension or a paste, or by adding it to a liquid drink or feed for animals. In the case of parenteral administration, the present parasiticide can be applied in the form of an injection, drops, suppositories, an emulsion, a suspension, an ointment, a cream, a solution, a lotion, a spray, an aerosol, a cataplasma or a tape, or in a form allowing for mucosity or percutaneous absorption.

The present parasiticide is effective to endoparasites when administered singly. It can also be used in combination with other known parasite drugs for humans and animals and, in this case, an synergistic effect can be expected and the respective doses may be lowered.

When the present parasiticide for endoparasites is used as a drug for humans and animals, the optimum dose varies depending upon the various factors such as the application purpose (cure or prevention), the kind of target parasite, the type and degree of infection and the form in which the parasiticide is applied. However, the dose is generally about 0.001–10,000 mg per kg (body weight) per day in the case of oral administration, and is generally about 0.001–10,000 mg per kg per day in the case of parenteral administration. Said daily dose is applied in one portion or several portions.

The concentration of the natural or synthetic pyrethroid type compound in the present parasiticide for endoparasites is generally about 0.01–99% by weight, preferably about 0.01–20% by weight. The present parasiticide for endoparasites can also be provided as a high concentration composition which is diluted, when used, into an appropriate concentration with an appropriate diluent.

The present invention will hereinafter be described in detail by Examples of the present parasiticide for endoparasites and Test Examples when the present parasiticide was applied. These Examples and Test Examples show the effects of the present invention but do not restrict the scope.

The synthetic pyrethroid type compounds used in the Examples and Test Examples were as follows.

Compound 1: etofenprox=2-(4-ethoxyphenyl)-2-methylpropyl 3-phenoxybenzyl ether

Compound 2: MTI-790=1-(3-phenoxyphenyl)-4-(4-ethoxyphenyl)-4-methylpentane

Compound 3: MTI-800=1-(3-phenoxy-4-fluorophenyl)-4-(4-ethoxyphenyl)-4-methylpentane Compound 4: HOE-498=(4-ethoxyphenyl) [3-(4-fluoro-3-phenoxyphenyl)propyl] (dimethyl) silane

EXAMPLE 1

Emulsion 10 parts by weight of the compound 1, 2, 3 or and 6 parts by weight of an emulsifier (Sorpol 355F, a product of Toho Chemical Industries, Co., Ltd.) are dissolved in 84 parts by weight of xylene to obtain an emulsion.

EXAMPLE 2

Ointment 1 part by weight of the compound 1, 50 parts by weight of bleached bees wax and 49 parts by weight of white vaseline are mixed thoroughly to obtain an ointment.

EXAMPLE 3

Tablets 2 parts by weight of the compound 1, 10 parts by weight of a vegetable oil (olive oil), 3 parts by weight of crystalline cellulose, 20 parts by weight of white carbon and 65 parts by weight of kaolin are mixed thoroughly and made into tablets.

EXAMPLE 4

Injection 10 parts by weight of the compound 1, 10 parts by weight of propylene glycol of food additive grade and 80 parts by weight of a vegetable oil (corn oil) are mixed to obtain an injection.

EXAMPLE 5

Aqueous agent 5 parts by weight of the compound 1, 2 or 3, 20 parts by weight of a surfactant (Tween 80) and 75 parts by weight of deionized water are mixed thoroughly to obtain an aqueous agent.

Test Example 1

Test for anti-microfilaria activity

The microfilariae collected from the abdominal cavity of a microfilaria-infected Mongolian gerbil were incubated in a liquid medium containing the compound 1. After given periods, the parasiticidal effects of the compound 1 were examined. The results are shown in Table 1.

TABLE 1

| Days after administration | Extermination ratio (%) Conc. of compound 1 in medium (ppm) | | |
|---|---|---|---|
| | 0 | 10 | 20 |
| 1 | 0 | 0 | 0 |
| 8 | 1 | 0 | 13 |
| 14 | 9 | 60 | 83 |

As is clear from Table 1, the compound 1 has a parasiticidal effect on microfilariae.

Test Example 2

Test for Plasmodium spp. (malaria parasite)

The compounds 1, 2, 3 and 4 were separately dissolved in corn oil. Each solution was orally or percutaneously administered to a group of five mice infected with malaria. The mortality of mice was observed with the lapse of time. The results are shown Table 2 and Table 3.

TABLE 2

Results of oral administration

| Compound No. | Dose (mg/mouse) | Mortality (%) Days lapsed | | | | |
|---|---|---|---|---|---|---|
| | | 1 | 3 | 7 | 10 | 14 |
| 1 | 5.0 | 0 | 0 | 0 | 0 | 0 |
| | 25.0 | 0 | 0 | 0 | 0 | 0 |
| 2 | 5.0 | 0 | 0 | 0 | 0 | 0 |
| | 25.0 | 0 | 0 | 0 | 0 | 0 |
| 3 | 5.0 | 0 | 0 | 0 | 0 | 0 |
| | 25.0 | 0 | 0 | 0 | 0 | 0 |
| 4 | 5.0 | 0 | 0 | 0 | 0 | 0 |
| | 25.0 | 0 | 0 | 0 | 0 | 0 |
| Untreated | — | 0 | 0 | 100 | — | — |

TABLE 3

Results of percutaneous administration

| Compound No. | Dose (mg/mouse) | Mortality (%) Days lapsed | | | | |
|---|---|---|---|---|---|---|
| | | 1 | 3 | 7 | 10 | 14 |
| 1 | 1.0 | 0 | 0 | 0 | 0 | 0 |
| | 5.0 | 0 | 0 | 0 | 0 | 0 |
| 2 | 1.0 | 0 | 0 | 0 | 0 | 0 |
| | 5.0 | 0 | 0 | 0 | 0 | 0 |
| 3 | 1.0 | 0 | 0 | 0 | 0 | 0 |
| | 5.0 | 0 | 0 | 0 | 0 | 0 |
| 4 | 1.0 | 0 | 0 | 0 | 0 | 0 |
| | 5.0 | 0 | 0 | 0 | 0 | 0 |
| Untreated | — | 0 | 0 | 100 | — | — |

As is clear from Table 2 and Table 3, all of the compounds 1, 2, 3 and 4 show an life-prolonging effect on malaria-affected mice in both oral administration and percutaneous administration.

Test Example 3 Effects on *Toxocara canis* and *Ancylostoma caninum*

Dog excrements were tested by the formalinether method to examine the presence of parasites (*Toxocara canis* and *Ancylostoma caninum*) in their digestive canals, whereby dogs infected with these parasites were selected. The number of dogs which showed "egg-positive" and the kinds of parasites in these dogs are shown in Table 4. The compound 1 was suspended in a given amount of corn oil and orally administered to the selected dogs. After the administration, dogs excrements were tested daily to examine the presence of parasites. On the seventh day from the administration, excrements were tested by the formalinether method to examine the presence of eggs (*Toxocara canis*) and adults (*Ancylostoma caninum*). The effects of the compound 1 on *Toxocara canis* are shown in Table 5, and the effects of the compound 1 on *Ancylostoma caninum* are shown in Table 6.

TABLE 4

| Kind of parasites | Number of dogs which showed egg-positive |
|---|---|
| *Toxocara canis* | 13 |
| *Ancylostoma caninum* | 8 |

TABLE 5

| | Number of dogs | | |
|---|---|---|---|
| Dose (mg/kg) | Administered dogs | Parasite-exterminated dogs | Extermination Ratio (%) |
| 50 | 7 | 7 | 100 |
| 250 | 6 | 6 | 100 |

TABLE 6

| | Number of dogs | | |
|---|---|---|---|
| Dose (mg/kg) | Administered dogs | Parasite-exterminated dogs | Extermination Ratio (%) |
| 50 | 4 | 4 | 100 |
| 250 | 4 | 4 | 100 |

The administration of the compound 1 in amounts of 50 mg/kg and 250 mg/kg achieved the complete extermination of *Toxocara canis* and *Ancylostoma caninum*.

Test Example 4

Effect on filaria

Mongolian gerbils were infected with filariae (*Brugia pahangi*). From the fifth day from the infection, the compound 1 dissolved in corn oil was percutaneously administered to the mongolian gerbils for 5 consecutive days at a dose of 20 mg per kg per day. At given intervals, blood was collected from the mongolian gerbils and examined for number of microfilariae present therein. The results are shown in Table 7.

TABLE 7

| Weeks after infection | Microfilariae (number/10 μl) | |
| --- | --- | --- |
| | Untreated | Compound 1 |
| 9 | 0 | 0 |
| 14 | 18 | 5 |
| 16 | 38 | 4 |
| 19 | 27 | 3 |

As is clear from Table 7, the compound 1 is effective for the extermination of filariae (*Bruqia pahangi*) present in Mongolian gerbils and the effect was lasting.

As is clear from the above Test Examples, the parasiticide containing the present compound exhibits an excellent effect to various parasites when administered orally or percutaneously.

What is claimed is:

1. A method for exterminating malaria parasite which comprises orally or percutaneously administering to a human or animal a parasiticide comprising 2-(4-ethoxyphenyl)-2-methylpropyl 3-phenoxybenzyl ether in an amount effective for exterminating malaria parasite.

2. A method for exterminating malaria parasites according to claim 1, wherein said parasiticide is administered in an amount between about 0.001 and 10,000 mg/kg of body weight/day.

3. A method for exterminating malaria parasites according to claim 2, wherein said 2-(4-ethoxyphenyl)-2-methylpropyl 3-phenoxybenzyl ether is present in an amount between about 0.01 and 99% by weight.

4. A method for exterminating malaria parasites according to claim 3, wherein said 2-(4-ethoxyphenyl)-2-methylpropyl 3-phenoxybenzyl ether is present in an amount between about 0.01 and 20% by weight.

\* \* \* \* \*